United States Patent
Kisiday et al.

(10) Patent No.: US 7,449,180 B2
(45) Date of Patent: Nov. 11, 2008

(54) MACROSCOPIC SCAFFOLD CONTAINING AMPHIPHILIC PEPTIDES ENCAPSULATING CELLS

(76) Inventors: John Kisiday, 805 Mount Auburn St. G4, Watertown, MA (US) 02472; Alan Grodzinsky, 31 Tyler Rd., Lexington, MA (US) 02173; Shuguang Zhang, 25 Bowker St., Lexington, MA (US) 02421-4142

( * ) Notice: Subject to any disclaimer, the term of this patent is extended or adjusted under 35 U.S.C. 154(b) by 0 days.

(21) Appl. No.: 09/778,200

(22) Filed: Feb. 6, 2001

(65) Prior Publication Data

US 2002/0160471 A1   Oct. 31, 2002

(51) Int. Cl.
*C07K 1/00* (2006.01)
*C12N 11/02* (2006.01)
*C12N 5/00* (2006.01)

(52) U.S. Cl. .............. 424/93.7; 424/426; 435/177; 435/395; 530/402

(58) Field of Classification Search ............ 424/423, 424/93.7; 435/177, 395; 530/402
See application file for complete search history.

(56) References Cited

U.S. PATENT DOCUMENTS

| | | | | |
|---|---|---|---|---|
| 5,175,093 | A | * | 12/1992 | Seifert ............... 435/41 |
| 5,472,869 | A | * | 12/1995 | Krzyzek et al. .......... 435/412 |
| 5,670,483 | A | | 9/1997 | Zhang et al. ............. 514/14 |
| 5,786,217 | A | | 7/1998 | Tubo et al. ............. 435/402 |
| 5,904,717 | A | | 5/1999 | Brekke et al. ............. 623/16 |
| 5,955,343 | A | | 9/1999 | Holmes et al. .......... 435/240.1 |
| 6,129,761 | A | * | 10/2000 | Hubbell ............... 623/11 |
| 6,306,169 | B1 | * | 10/2001 | Lee et al. ............. 623/11.11 |
| 6,344,488 | B1 | * | 2/2002 | Chenite et al. ........... 514/777 |

OTHER PUBLICATIONS

Buschmann et al., "Mechanical compression modulates matrix biosynthesis in chondrocyte/agarose culture," *J. of Cell Science* 108:1497-1508 (1995).
Holmes et al., "Extensive neurite outgrowth and active synapse formation on self-assembling peptide scaffolds," *PNAS* 97:6728-6733 (2000).
Kisiday et al., "Self-assembling peptide scaffold for cartilage tissue engineering," Orthopaedic Research Society, California (abstract) (2001).
Kisiday et al., "A new self-assembling peptide gel for cartilage tissue engineering: chondrocyte encapsulation and matrix production," *International Cartilage Repair Society*, Sweden (poster) (2000).
Kisiday et al., "A new self-assembling peptide gel for cartilage tissue engineering: chondrocyte encapsulation and matrix production," International Cartilage Repair Society, Sweden (abstract) (2000).
Kisiday et al., "Cartilage tissue engineering using a new self-assembling peptide gel," Biomedical Engineering Society Annual Meeting, Seattle (2000).
Leon et al., "Mechanical properties of a self-assembling oligopeptide matrix," *J. Biomater. Sci. Polymer Edn.* 9:297-312 (1998).
Schachner, "Nervous engineering," *Nature* 405:747-748 (2000).
Schwartz et al., "Peptide-mediated cellular delivery," *Current Opinion in Molecular Therapeutics* 2:162-167 (2000).
Zhang et al., "Spontaneous assembly of a self-complementary oligopeptide to form a stable macroscopic membrane," *Proc. Natl. Acad. Sci. U.S.A.* 90:3334-3338 (1993).
Zhang et al., "Biological surface engineering: a simple system for cell pattern formation," *Biomaterials* 20:1213-1220 (1999).
Zhang et al., "Zuotin, a putative Z-DNA binding protein in *Saccharomyces cerevisiae*," *EMBO J.* 3787-3796 (1992).
Zhang et al., "Peptide self-assembly in functional polymer science and engineering," *Reactive & Functional Polymers* 41:91-102 (1999).
Zhang et al., "Direct conversion of an oligopeptide from a β-sheet to an α-helix: A model for amyloid formation," *Proc. Natl. Acad. Sci. U.S.A.* 94:23-28 (1997).
Zhang et al., "Self-complementary oligopeptide matrices support mammalian cell attachment," *Biomaterials* 16:1385-1393 (1995).
Aggeli, et al., "Responsive gels formed by the spontaneous self-assembly of peptides into polymetric β-sheet tapes", Nature, 386:260-262, 1997.
Kisiday, et al., "Self-assembling peptide hydrogel fosters chondrocyte extracellular matrix production and cell division: Implications for cartilage tissue repair", Proc. Natl. Acad. Sci., 99(15):9996-1001, 2002.

* cited by examiner

*Primary Examiner*—David M Naff

(57) ABSTRACT

The invention features peptide scaffolds that are useful in the repair and replacement of various tissues. The invention also provides methods for making these scaffolds and methods for using them.

26 Claims, 9 Drawing Sheets

SEQUENCE LISTING

<160> NUMBER OF SEQ ID NOS: 43

<210> SEQ ID NO 1
<211> LENGTH: 16
<212> TYPE: PRT
<213> ORGANISM: Artificial Sequence
<220> FEATURE:
<223> OTHER INFORMATION: Designed Peptide

<400> SEQUENCE: 1

-continued

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Designed Peptide

<400> SEQUENCE: 2

Arg Ala Asp Ala Arg Gly Asp Ala Arg Ala Asp Ala Arg Gly Asp Ala
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Designed Peptide

<400> SEQUENCE: 3

Arg Ala Asp Ala Arg Ala Asp Ala
1               5

<210> SEQ ID NO 4
<211> LENGTH: 16
<212> TYPE: PRT
<213> ORGANISM: Artificial Sequence
<220> FEATURE:
<223> OTHER INFORMATION: Designed Peptide

<400> SEQUENCE: 4

Arg Ala Arg Ala Asp Ala Asp Ala Arg Ala Arg Ala Asp Ala Asp Ala
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Designed Peptide

<400> SEQUENCE: 5

Arg Ala Arg Ala Asp Ala Asp Ala
1               5

<210> SEQ ID NO 6
<211> LENGTH: 16
<212> TYPE: PRT
<213> ORGANISM: Artificial Sequence
<220> FEATURE:
<223> OTHER INFORMATION: Designed Peptide

<400> SEQUENCE: 6

Ala Glu Ala Lys Ala Glu Ala Lys Ala Glu Ala Lys Ala Glu Ala Lys
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Designed Peptide

<400> SEQUENCE: 7

Ala Glu Ala Lys Ala Glu Ala Lys

<210> SEQ ID NO 8
<211> LENGTH: 16
<212> TYPE: PRT
<213> ORGANISM: Artificial Sequence
<220> FEATURE:
<223> OTHER INFORMATION: Designed Peptide

<400> SEQUENCE: 8

Arg Ala Glu Ala Arg Ala Glu Ala Arg Ala Glu Ala Arg Ala Glu Ala
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: Designed Peptide

<400> SEQUENCE: 9

Arg Ala Glu Ala Arg Ala Glu Ala
1               5

<210> SEQ ID NO 10
<211> LENGTH: 16
<212> TYPE: PRT
<213> ORGANISM: Artificial Sequence
<220> FEATURE:
<223> OTHER INFORMATION: Designed Peptide

<400> SEQUENCE: 10

Lys Ala Asp Ala Lys Ala Asp Ala Lys Ala Asp Ala Lys Ala Asp Ala
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Designed Peptide

<400> SEQUENCE: 11

Lys Ala Asp Ala Lys Ala Asp Ala
1               5

<210> SEQ ID NO 12
<211> LENGTH: 16
<212> TYPE: PRT
<213> ORGANISM: Artificial Sequence
<220> FEATURE:
<223> OTHER INFORMATION: Designed Peptide

<400> SEQUENCE: 12

Ala Glu Ala Glu Ala His Ala His Ala Glu Ala Glu Ala His Ala His
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: Designed Peptide

<400> SEQUENCE: 13

Ala Glu Ala Glu Ala His Ala His
1               5

-continued

```
<210> SEQ ID NO 14
<211> LENGTH: 16
<212> TYPE: PRT
<213> ORGANISM: Artificial Sequence
<220> FEATURE:
<223> OTHER INFORMATION: Designed Peptide

<400> SEQUENCE: 14

Phe Glu Phe Glu Phe Lys Phe Lys Phe Glu Phe Glu Phe Lys Phe Lys
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Designed Peptide

<400> SEQUENCE: 15

Phe Glu Phe Lys Phe Glu Phe Lys
1               5

<210> SEQ ID NO 16
<211> LENGTH: 16
<212> TYPE: PRT
<213> ORGANISM: Artificial Sequence
<220> FEATURE:
<223> OTHER INFORMATION: Designed Peptide

<400> SEQUENCE: 16

Leu Glu Leu Glu Leu Lys Leu Lys Leu Glu Leu Glu Leu Lys Leu Lys
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: Designed Peptide

<400> SEQUENCE: 17

Leu Glu Leu Glu Leu Lys Leu Lys
1               5

<210> SEQ ID NO 18
<211> LENGTH: 16
<212> TYPE: PRT
<213> ORGANISM: Artificial Sequence
<220> FEATURE:
<223> OTHER INFORMATION: Designed Peptide

<400> SEQUENCE: 18

Ala Glu Ala Glu Ala Lys Ala Lys Ala Glu Ala Glu Ala Lys Ala Lys
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Designed Peptide

<400> SEQUENCE: 19

Ala Glu Ala Glu Ala Glu Ala Glu Ala Lys Ala Lys
1               5                   10
```

```
<210> SEQ ID NO 20
<211> LENGTH: 8
<212> TYPE: PRT
<213> ORGANISM: Artificial Sequence
<220> FEATURE:
<223> OTHER INFORMATION: Designed Peptide

<400> SEQUENCE: 20

Ala Glu Ala Glu Ala Lys Ala Lys
 1               5

<210> SEQ ID NO 21
<211> LENGTH: 16
<212> TYPE: PRT
<213> ORGANISM: Artificial Sequence
<220> FEATURE:
<223> OTHER INFORMATION: Designed Peptide

<400> SEQUENCE: 21

Lys Ala Lys Ala Lys Ala Lys Ala Glu Ala Glu Ala Glu Ala Glu Ala
 1               5                  10                  15

<210> SEQ ID NO 22
<211> LENGTH: 16
<212> TYPE: PRT
<213> ORGANISM: Artificial Sequence
<220> FEATURE:
<223> OTHER INFORMATION: Designed Peptide

<400> SEQUENCE: 22

Ala Glu Ala Glu Ala Glu Ala Glu Ala Lys Ala Lys Ala Lys Ala Lys
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Designed Peptide

<400> SEQUENCE: 23

Arg Ala Arg Ala Arg Ala Arg Ala Asp Ala Asp Ala Asp Ala Asp Ala
 1               5                  10                  15

<210> SEQ ID NO 24
<211> LENGTH: 16
<212> TYPE: PRT
<213> ORGANISM: Artificial Sequence
<220> FEATURE:
<223> OTHER INFORMATION: Designed Peptide

<400> SEQUENCE: 24

Ala Asp Ala Asp Ala Asp Ala Asp Ala Arg Ala Arg Ala Arg Ala Arg
 1               5                  10                  15

<210> SEQ ID NO 25
<211> LENGTH: 16
<212> TYPE: PRT
<213> ORGANISM: Artificial Sequence
<220> FEATURE:
<223> OTHER INFORMATION: Designed Peptide

<400> SEQUENCE: 25

Asp Ala Asp Ala Asp Ala Asp Ala Arg Ala Arg Ala Arg Ala Arg Ala
 1               5                  10                  15
```

<210> SEQ ID NO 26
<211> LENGTH: 16
<212> TYPE: PRT
<213> ORGANISM: Artificial Sequence
<220> FEATURE:
<223> OTHER INFORMATION: Designed Peptide

<400> SEQUENCE: 26

Ala Asp Ala Asp Ala Asp Ala Asp Ala Arg Ala Arg Ala Arg Ala Arg
 1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: Designed Peptide

<400> SEQUENCE: 27

His Glu His Glu His Lys His Lys His Glu His Glu His Lys His Lys
 1               5                  10                  15

<210> SEQ ID NO 28
<211> LENGTH: 8
<212> TYPE: PRT
<213> ORGANISM: Artificial Sequence
<220> FEATURE:
<223> OTHER INFORMATION: Designed Peptide

<400> SEQUENCE: 28

His Glu His Glu His Lys His Lys
 1               5

<210> SEQ ID NO 29
<211> LENGTH: 20
<212> TYPE: PRT
<213> ORGANISM: Artificial Sequence
<220> FEATURE:
<223> OTHER INFORMATION: Designed Peptide

<400> SEQUENCE: 29

Val Glu Val Glu Val Glu Val Glu Val Glu Val Glu Val Glu Val Glu
 1               5                  10                  15

Val Glu Val Glu
            20

<210> SEQ ID NO 30
<211> LENGTH: 20
<212> TYPE: PRT
<213> ORGANISM: Artificial Sequence
<220> FEATURE:
<223> OTHER INFORMATION: Designed Peptide

<400> SEQUENCE: 30

Arg Phe Arg Phe Arg Phe Arg Phe Arg Phe Arg Phe Arg Phe Arg Phe
 1               5                  10                  15

Arg Phe Arg Phe
            20

<210> SEQ ID NO 31
<211> LENGTH: 16
<212> TYPE: PRT
<213> ORGANISM: Artificial Sequence
<220> FEATURE:
<223> OTHER INFORMATION: Designed Peptide

<400> SEQUENCE: 31

Arg Gly Asp Tyr Arg Tyr Asp Tyr Arg Tyr Asp Tyr Arg Gly Asp Tyr
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Designed Peptide

<400> SEQUENCE: 32

Arg Gly Asp Phe Arg Phe Asp Phe Arg Phe Asp Phe Arg Gly Asp Phe
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Designed Peptide

<400> SEQUENCE: 33

Arg Gly Asp Trp Arg Trp Asp Trp Arg Trp Asp Trp Arg Gly Asp Trp
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Designed Peptide

<400> SEQUENCE: 34

Arg Ala Asp Tyr Arg Tyr Glu Tyr Arg Tyr Glu Tyr Arg Ala Asp Tyr
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Designed Peptide

<400> SEQUENCE: 35

Arg Ala Asp Phe Arg Phe Asp Phe Arg Phe Asp Phe Arg Ala Asp Phe
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Designed Peptide

<400> SEQUENCE: 36

Arg Ala Asp Trp Arg Trp Asp Trp Arg Trp Asp Trp Arg Ala Asp Trp
1               5                   10                  15

<210> SEQ ID NO 37
<211> LENGTH: 26
<212> TYPE: PRT
<213> ORGANISM: Artificial Sequence
<220> FEATURE:
<223> OTHER INFORMATION: Designed Peptide

<400> SEQUENCE: 37

Arg Gly Asp Tyr Arg Tyr Asp Tyr Thr Phe Arg Glu Glu Gly Leu
1               5                   10                  15

Gly Ser Arg Tyr Asp Tyr Arg Gly Asp Tyr
            20                  25

<210> SEQ ID NO 38
<211> LENGTH: 26
<212> TYPE: PRT
<213> ORGANISM: Artificial Sequence
<220> FEATURE:
<223> OTHER INFORMATION: Designed Peptide

<400> SEQUENCE: 38

Arg Gly Asp Tyr Arg Tyr Asp Tyr Thr Phe Lys Glu Glu Gly Leu
1               5                   10                  15

Gly Ser Arg Tyr Asp Tyr Arg Gly Asp Tyr
            20                  25

<210> SEQ ID NO 39
<211> LENGTH: 26
<212> TYPE: PRT
<213> ORGANISM: Artificial Sequence
<220> FEATURE:
<223> OTHER INFORMATION: Designed Peptide

<400> SEQUENCE: 39

Arg Gly Asp Tyr Arg Tyr Asp Tyr Thr Ala Ser Glu Leu Glu Gly Arg
1               5                   10                  15

Gly Thr Arg Tyr Asp Tyr Arg Gly Asp Tyr
            20                  25

<210> SEQ ID NO 40
<211> LENGTH: 27
<212> TYPE: PRT
<213> ORGANISM: Artificial Sequence
<220> FEATURE:
<223> OTHER INFORMATION: Designed Peptide

<400> SEQUENCE: 40

Arg Gly Asp Tyr Arg Tyr Asp Tyr Ala Pro Thr Ala Gln Glu Ala Gly
1               5                   10                  15

Glu Gly Pro Arg Tyr Asp Tyr Arg Gly Asp Tyr
            20                  25

<210> SEQ ID NO 41
<211> LENGTH: 27
<212> TYPE: PRT
<213> ORGANISM: Artificial Sequence
<220> FEATURE:
<223> OTHER INFORMATION: Designed Peptide

<400> SEQUENCE: 41

Arg Gly Asp Tyr Arg Tyr Asp Tyr Pro Thr Ile Ser Gln Glu Leu Gly
1               5                   10                  15

Gln Arg Pro Arg Tyr Asp Tyr Arg Gly Asp Tyr
            20                  25

<210> SEQ ID NO 42
<211> LENGTH: 27
<212> TYPE: PRT
<213> ORGANISM: Artificial Sequence
<220> FEATURE:
<223> OTHER INFORMATION: Designed Peptide

<400> SEQUENCE: 42

```
Arg Gly Asp Tyr Arg Tyr Asp Tyr Pro Thr Val Ser Gln Glu Leu Gly
 1               5                  10                  15

Gln Arg Pro Arg Tyr Asp Tyr Arg Gly Asp Tyr
            20                  25

<210> SEQ ID NO 43
<211> LENGTH: 12
<212> TYPE: PRT
<213> ORGANISM: Artificial Sequence
<220> FEATURE:
<223> OTHER INFORMATION: Designed Peptide

<400> SEQUENCE: 43

Lys Leu Asp Leu Lys Leu Asp Leu Lys Leu Asp Leu
 1               5                  10
```

MACROSCOPIC SCAFFOLD CONTAINING AMPHIPHILIC PEPTIDES ENCAPSULATING CELLS

STATEMENT AS TO FEDERALLY SPONSORED RESEARCH

This invention was made with government support under NIH grants AR45779 and AR33236. The government therefore has certain rights in the invention.

BACKGROUND OF THE INVENTION

During the past decade there has been substantial effort expended to develop materials for the repair and replacement of various tissues, especially cartilage tissue in the knee joint. Although various polymeric biomaterials have been developed for tissue repair, these biomaterials suffer from immune incompatibility and improper distribution of stress. Furthermore, the use of material from animals, such as cow hide or cartilage from pigs or sharks, has raised concerns of possible contamination by infectious agents, such as prions. Thus, improved materials of biological origin that have improved compatibility, present a reduced risk of contamination, and provide the proper biomechanical characteristics for tissue repair are needed. In addition, these materials will preferably promote the interaction between native tissue and implanted cells. The ability to control the rate of biodegradation of these material is also desirable.

SUMMARY OF THE INVENTION

The purpose of the present invention is to provide improved biomaterials and methods for tissue repair or replacement. We discovered that living cells may be encapsulated by a biodegradable peptide scaffold in a three-dimensional arrangement of predetermined geometry. The secretion of extracellular matrix components by the encapsulated cells significantly increases the stiffness of the scaffolds and thereby improves the ability of the scaffold to repair or replace endogenous cartilage.

Accordingly, in one aspect, the invention features a macroscopic scaffold having amphiphilic peptides. The peptides have alternating hydrophobic and hydrophilic amino acids, are complementary and structurally compatible, and self-assemble into a beta-sheet macroscopic scaffold. The macroscopic scaffold encapsulates living cells, and the encapsulated cells are present in the macroscopic scaffold in a three-dimensional arrangement.

In another aspect, the invention features a method of forming a macroscopic scaffold. This method involves incubating peptides and living cells in an aqueous solution having an iso-osmotic solute, preferably under conditions that do not allow the peptides to substantially self-assemble. Preferably, the solution contains less than 10, 5, 1, or 0.1 mM electrolyte or is substantially free of electrolyte. The peptides have alternating hydrophobic and hydrophilic amino acids and are complementary and structurally compatible. Sufficient electrolyte is added to the solution to initiate self-assembly of the peptides into a beta-sheet macroscopic scaffold, whereby the cells are encapsulated by the formation of the macroscopic scaffold. The encapsulated cells are present in the macroscopic scaffold in a three-dimensional arrangement. Preferably, the concentration of the added electrolyte is at least 5, 10, 20, or 50 mM. Preferred electrolytes include $Li^+$, $Na^+$, $K^+$, and $Cs^+$. In one preferred embodiment, the concentration of the iso-osmotic solute is at least 50, 150, or 300 mM. In another preferred embodiment, the concentration of the iso-osmotic solute is contained in one of the following ranges 200 to 250 mM, 250 to 270 mM, 270 to 300 mM, 300 to 400 mM, 400 to 500 mM, 500 to 600 mM, 600 to 700 mM, 700 to 800 mM, or 800 to 900 mM, inclusive. Preferred iso-osmotic solutes include carbohydrates, such as monosaccharides or disaccharides. Examples of preferred carbohydrates include sucrose, glucose, galactose, fructose, ribose, mannose, arabinose, and xylose. Still another preferred iso-osmotic solute is glycerol, such an aqueous solution of glycerol that is between 5 to 20% (v/v) glycerol.

In yet another aspect, the invention provides a method of forming a macroscopic scaffold of predetermined shape or volume. This method includes incubating peptides and living cells in an aqueous solution having an iso-osmotic solute, preferably under conditions that do not allow the peptides to substantially self-assemble. Preferably, the solution contains less than 10, 5, 1, or 0.1 mM electrolyte or is substantially free of electrolytes. The solution is contained in a pre-shaped mold dimensioned to determine the volume or shape of the macroscopic scaffold. The peptides have alternating hydrophobic and hydrophilic amino acids and are complementary and structurally compatible. Sufficient electrolyte is added to the solution to initiate self-assembly of the peptides into a beta-sheet macroscopic scaffold, whereby the cells are encapsulated by the formation of the macroscopic scaffold. The encapsulated cells are present in the macroscopic scaffold in a three-dimensional arrangement. Preferably, the concentration of the added electrolyte is at least 5, 10, 20, or 50 mM. Preferred electrolytes include $Li^+$, $Na^+$, $K^+$, and $Cs^+$. In one preferred embodiment, the concentration of the iso-osmotic solute is at least 50, 150, or 300 mM. In another preferred embodiment, the concentration of the iso-osmotic solute is contained in one of the following ranges 200 to 250 mM, 250 to 270 mM, 270 to 300 mM, 300 to 400 mM, 400 to 500 mM, 500 to 600 mM, 600 to 700 mM, 700 to 800 mM, or 800 to 900 mM, inclusive. Preferred iso-osmotic solutes include carbohydrates, such as monosaccharides or disaccharides. Examples of preferred carbohydrates include sucrose, glucose, galactose, fructose, ribose, mannose, arabinose, and xylose. Still another preferred iso-osmotic solute is glycerol, such an aqueous solution of glycerol that is between 5 to 20% (v/v) glycerol.

In still another aspect, the invention features a method of regenerating a tissue. This method includes administering to a mammal a macroscopic scaffold having amphiphilic peptides and encapsulated living cells. The peptides have alternating hydrophobic and hydrophilic amino acids, are complementary and structurally compatible, and self-assemble into a beta-sheet macroscopic scaffold. The encapsulated cells are present in the macroscopic scaffold in a three-dimensional arrangement. Preferably, the method is used to treat or prevent a cartilage defect, connective tissue defect, nervous tissue defect, epidermal lining defect, endothelial lining defect, or arthritis. A preferred connective tissue is a ligament or tendon, and a preferred epidermal lining is skin. Preferably, the cells are autologogous or allogeneic. Preferred routes of administration include oral, percutaneous, intramuscular, intravenous, subcutaneous, and surgical. A preferred surgical administration is arthroscopic surgery. Preferably, the mammal is human.

In a related aspect, the invention provides another method of regenerating a tissue. This method involves administering to a mammal a solution having amphiphilic peptides, living cells, and an iso-osmotic solute. The peptides have alternating hydrophobic and hydrophilic amino acids and are complementary and structurally compatible. The peptides do not substantially self-assemble prior to administration, but they self-assemble into a beta-sheet macroscopic scaffold after administration to the mammal. The formation of the macroscopic scaffold encapsulates the cells in vivo, and the encapsulated cells are present in the macroscopic scaffold in a three-dimensional arrangement. Preferably, the administered solution contains less than 10, 5, 1.0, or 0.1 mM electrolyte or is substantially free of electrolyte. Preferably, the concentration of the iso-osmotic solute is at least 50, 150, or 300 mM. In another preferred embodiment, the concentration of iso-osmotic solute is contained in one of the following ranges 200 to 250 mM, 250 to 270 mM, 270 to 300 mM, 300 to 400 mM, 400 to 500 mM, 500 to 600 mM, 600 to 700 mM, 700 to 800 mM, or 800 to 900 mM, inclusive. Preferred iso-osmotic solutes include carbohydrates, such as monosaccharides or disaccharides. Examples of preferred carbohydrates include sucrose, glucose, galactose, fructose, ribose, mannose, arabinose, and xylose. Still another preferred iso-osmotic solute is glycerol, such an aqueous solution of glycerol that is between 5 to 20% (v/v) glycerol. Preferably, this method is used to treat or prevent a cartilage defect, connective tissue defect, nervous tissue defect, epidermal lining defect, endothelial lining defect, or arthritis. A preferred connective tissue is a ligament or tendon, and a preferred epidermal lining is skin. Preferably, the cells are autologogous or allogeneic. Preferred routes of administration include oral, percutaneous, intramuscular, intravenous, subcutaneous, and surgical. A preferred surgical administration is arthroscopic surgery. Preferably, the mammal is human.

In preferred embodiments of various aspects of the invention, the macroscopic scaffold is enzymatically degradable. In other preferred embodiments, the macroscopic scaffold is cleaved by a metalloprotease, collagenase, or aggrecanase in vivo or in vitro. Preferably, an enzyme capable of cleaving the scaffold is produced by the encapsulating cells or nearby cells. In yet other preferred embodiments, the macroscopic scaffold further encapsulates a therapeutically active compound or chemoattractant. Examples of such therapeutically active compounds include synthetic organic molecules, naturally occurring organic molecules, nucleic acid molecules, biosynthetic proteins, or modified naturally occurring proteins. In still other preferred embodiments, the macroscopic scaffold further encapsulates a growth factor, such as a cartilage-derived growth factor, transforming growth factor-$\beta$, platelet derived growth factor, insulin-like growth factor, acidic fibroblast growth factor, basic fibroblast growth factor, epidermal growth factor, hepatocytic growth factor, keratinocyte growth factor, or bone morphogenic protein. Preferred macroscopic scaffolds have peptides which include an adhesion site, growth factor binding site, growth factor, or sequence that provides targeting to a cell, tissue, organ, organ system, or site within an mammal. Other preferred macroscopic scaffolds have a pre-determined volume or shape. In preferred embodiments, the encapsulated cells are substantially uniformly distributed. In other preferred embodiments, the encapsulated cells are neurons, and the macroscopic scaffold allows axonal outgrowth by the neurons. Preferably, the axons extend beyond the surface of the macroscopic scaffold. In yet other preferred embodiments, axons from neurons outside of the macroscopic scaffold extend into the macroscopic scaffold. In still other preferred embodiments, the cells differentiate after encapsulation by the macroscopic scaffold. Preferably, cells such as bone marrow cells, peristeal cells, perichondrial cells, or embryonic stem cells differentiate into cartilage cells. In other preferred embodiments, the cells are polypotent or pluripotent. In still yet other preferred embodiments, the cells are differentiated prior to encapsulation by the macroscopic scaffold and remain differentiated after the encapsulation. Preferred cells include chondrocytes, bone marrow cells, peristeal cells, perichondrial cells, fibroblasts, neuronal cells, hippocampal cells, epidermal cells, endothelial cells, keratinocytes, basal cells, spinous cells, granular cells, embryonic stem cells, ovarian cells, pancreatic cells, cervical cells, liver cells, and foreskin cells. The cells may be from any suitable source such as a human or bovine cells. Source of the cells may also include fetal or adult mammals or established cell lines.

Preferably, at least 40, 50, 60, 70, 80, 90, or 95% of the encapsulated cells are viable 1, 2, 4, 6, or more weeks after formation of the macroscopic scaffold. In another preferred embodiment, at least 80 or 90% of the encapsulated cells are viable one day or one week after formation of the macroscopic scaffold. More preferably, at least 90% or 95% of the encapsulated cells are viable 6 weeks after formation of the macroscopic scaffold. Preferably, the number of living cells encapsulated by the macroscopic scaffold five days after formation of the macroscopic scaffold is at least 1, 1.5, 3, 5, or 10 million per ml of the volume of the macroscopic scaffold. In another preferred embodiment, the number of living cells encapsulated by the macroscopic scaffold 3, 5, 10, 15, or more days after scaffold formation is at least 2, 3, 5, 10, or 20-fold greater than the initial number of encapsulated cells. In yet another preferred embodiment, at least 60, 70, 80, 90, or 95% of the encapsulated cells are in cell-cell contact with another encapsulated cell or with a cell outside of the scaffold.

In other preferred embodiments, the encapsulated cells secrete extracellular matrix components. Preferably, the secretion of extracellular matrix components increases the equilibrium compression modulus of the macroscopic scaffold by at least 5, 10, 20, 30, 50, 100, 200, 300, 400, or 500 kPA or by at least 2, 5, 25, 50, 75, or 100-fold. Preferably, the extracellular matrix secreted by a cell is in contact with the extracellular matrix secreted by another cell. More preferably, the extracellular matrix secreted by at least 60, 70, 80, 90, or 95% of the encapsulated cells is in contact with the extracellular matrix secreted by another encapsulated cell or secreted by a cell outside of the scaffold. Preferred macroscopic scaffolds further include a biodegradable sealant, glue, or polymer attached to the surface of the macroscopic scaffold that increases the equilibrium compression modulus of the macroscopic scaffold.

In preferred methods of the invention, the macroscopic scaffold is subjected to a predetermined compression scheme. For example, the macroscopic scaffold may be subjected to constant or variable pressure for a predetermined amount of time, such as for as few as 1, 2, or 3 weeks to as long as 6, 8, or more weeks. A preferred compression scheme includes dynamic compression at 0.01 to 3 Hz or more preferably 0.1 to 1 Hz, superimposed on a static offset compression. Typically, the dynamic strain amplitude is between 0.01 and 10%, preferably, between 1 and 5%, and, more preferably, between 3 and 5%, and the static offset compression is between 5 and 15%. Preferably, the compression scheme increases the equilibrium compression modulus of the macroscopic scaffold by at least 5, 10, 20, 30, 50, 100, 200, 300, 400, or 500 kPA or by at least 2, 5, 25, 50, 75, or 100-fold compared to a control macroscopic scaffold not subjected to the compression scheme. In another preferred embodiment, the compression scheme induces the secretion of extracellular matrix components by the cells.

Preferred peptides forming the macroscopic scaffold contain between 8 and 200 amino acids, 8 to 36 amino acids, or 8 to 16 amino acids, inclusive. Preferably, the concentration of the peptides is between 1 and 10 mg/ml or between 4 and 8 mg/ml, inclusive. Preferably, the macroscopic scaffold is preshaped to interfit a tissue defect. In one preferred embodiment, the tissue defect is in a joint, such as a knee, hip, shoulder, wrist, finger, ankle, toe, elbow, or neck. Preferably the tissue is an epithelial, connective, muscular, or nervous tissue. In one preferred embodiment, the cartilage is articular, costal, fibrous, hyaline, semilunar, thyroid, or elastic cartilage. In another preferred embodiment, the scaffold does not elicit an adverse immune or inflammatory response.

It is also contemplated that the methods of the present invention may be used to repair an injury to an organ or muscle or to form an organ or muscle. Preferred organs include the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, and uterus.

By "scaffold" is meant a three-dimensional structure capable of encapsulating cells. The beta-sheet secondary structure of the scaffold may be confirmed using standard circular dichroism to detect an absorbance minimum at approximately 218 nm and a maximum at approximately 195 nm. Preferably, the scaffold is formed from the self-assembly of peptides that include L-amino acids, D-amino acids, natural amino acids, non-natural amino acids, or a combination thereof. If L-amino acids are present in the scaffold, degradation of the scaffold produces amino acids which may be reused by the host tissue. It is also contemplated that the peptides may be covalently linked to a compound, such as a chemoattractant or a therapeutically active compound. The peptides may be chemically synthesized or purified from natural or recombinant sources, and the amino- and carboxytermini of the peptides may be protected or not protected. The peptide scaffold may be formed from one or more distinct molecular species of peptides which are complementary and structurally compatible with each other. Peptides containing mismatched pairs, such as the repulsive pairing of two similarly charged residues from adjacent peptides, may also form scaffolds if the disruptive force is dominated by stabilizing interactions between the peptides.

By "complementary" is meant the capable of forming ionic or hydrogen-bonding interactions between hydrophilic residues from adjacent peptides in the scaffold, as illustrated in FIG. 1. Preferably, each hydrophilic residue in a peptide either hydrogen-bonds or ionically pairs with a hydrophilic residue on an adjacent peptide or is exposed to solvent.

By "structurally compatible" is meant capable of maintaining a sufficiently constant interpeptide distance to allow scaffold formation. Preferably the variation in the interpeptide distance is less than 4, 3, 2, or 1 Å. It is also contemplated that larger variations in the interpeptide distance may not prevent scaffold formation if sufficient stabilizing forces are present. This distance may be calculated based on molecular modeling or based on a simplified procedure that has been previously reported (U.S. Pat. No. 5,670,483). In this method, the interpeptide distance is calculated by taking the sum of the number of unbranched atoms on the side-chains of each amino acid in a pair. For example, the interpeptide distance for a lysine-glutamic acid ionic pair is 5+4=9 atoms, and the distance for a glutamine-glutamine hydrogen-bonding pair is 4+4=8 atoms. Using a conversion factor of 3 Å per atom, the variation in the interpeptide distance of peptides having lysine-glutaminic acid pairs and glutamine-glutamine pairs (i.e., 9 versus 8 atoms) is 3 Å.

By "three-dimensional arrangement" is meant existing in three dimensions. Cells having a three-dimensional arrangement are not all part of the same monolayer. As used herein, a monolayer is a cross section through the peptide scaffold that has a thickness equal to the average diameter of the encapsulated cells and that includes at least one encapsulated cell. In one preferred embodiment, the encapsulated cells are neurons, and the average diameter of the neurons is determined by measuring the average diameter of the cell bodies of the neurons. An encapsulated cell is considered part of the monolayer if at least 51% of the volume of the cell is contained in the monolayer. Preferably, immediately after scaffold formation, at least one monolayer contains less than 75, 50, 25, 20, 15, 10, 5, or 1% (in order of preference) of the encapsulated cells. More preferably, immediately after scaffold formation, less than 75, 50, 25, 20, 15, 10, 5, or 1% (in order of preference) of the encapsulated cells are part of the same monolayer.

By "substantially uniformly distributed" is meant that immediately after scaffold formation the center of mass of at least 50, 60, 70, 80, 90, or 100% of the cells encapsulated by the scaffold are separated from each other by distances that vary by less than 500, 100, 50, 20, or 10 µM. Preferably, 1, 2, 3, or 4 weeks after scaffold formation, the center of mass of cell clusters or cell pairs for at least 50, 60, 70, 80, 90, or 100% of the encapsulated cells are separated from each other by distances that vary by less than 500, 100, 50, 20, or 10 µM.

By "iso-osmotic solute" is meant a non-ionizing compound dissolved in an aqueous solution.

By "solution that is substantially free of electrolytes" is meant a solution in which no electrolytes have been added or in which the concentration of electrolytes is less than 0.01 or 0.001 mM.

The present invention provides a number of advantages related to the repair or replacement of tissues. For example, these methods enable the encapsulation of living cells by a peptide scaffold in a three-dimensional arrangement and in a substantially uniform distribution, which may promote the viability and proliferation of the cells. The peptide scaffolds also have the advantage of not eliciting a detectable immune or inflammatory response in mammals. Further, the peptide scaffolds exhibited no detectable swelling when the scaffold was added to a saline solution. This lack of swelling is probably due to the high water content of the scaffold (>99%). This unique property of the scaffold reduces the probability of an unregulated expansion of the scaffold that could lead to adverse physiological effects on neighboring tissues. Moreover, if desired, the in vivo rate of degradation of the scaffolds may be modulated by the incorporation of protease cleavage sites into the scaffold. The secretion of extracellular matrix components by the encapsulated chondrocytes increased the stiffness of the scaffold by over 50-fold, improving the ability of the scaffold to be used to replace endogenous cartilage. Furthermore, adding growth factors to the scaffold to stimulate the chondrocytes, compressing the scaffold, or increasing the initial concentrations of the cells or peptides may further increase the stiffness of the scaffold.

Other features and advantages of the invention will be apparent from the following detailed description and from the claims.

BRIEF DESCRIPTION OF THE DRAWINGS

As illustrated in FIG. 9C, a peptide scaffold was also fabricated in the shape of a sheet. A centimeter scale is shown below the sheet structure in FIG. 9C.

DETAILED DESCRIPTION

Figure 1:
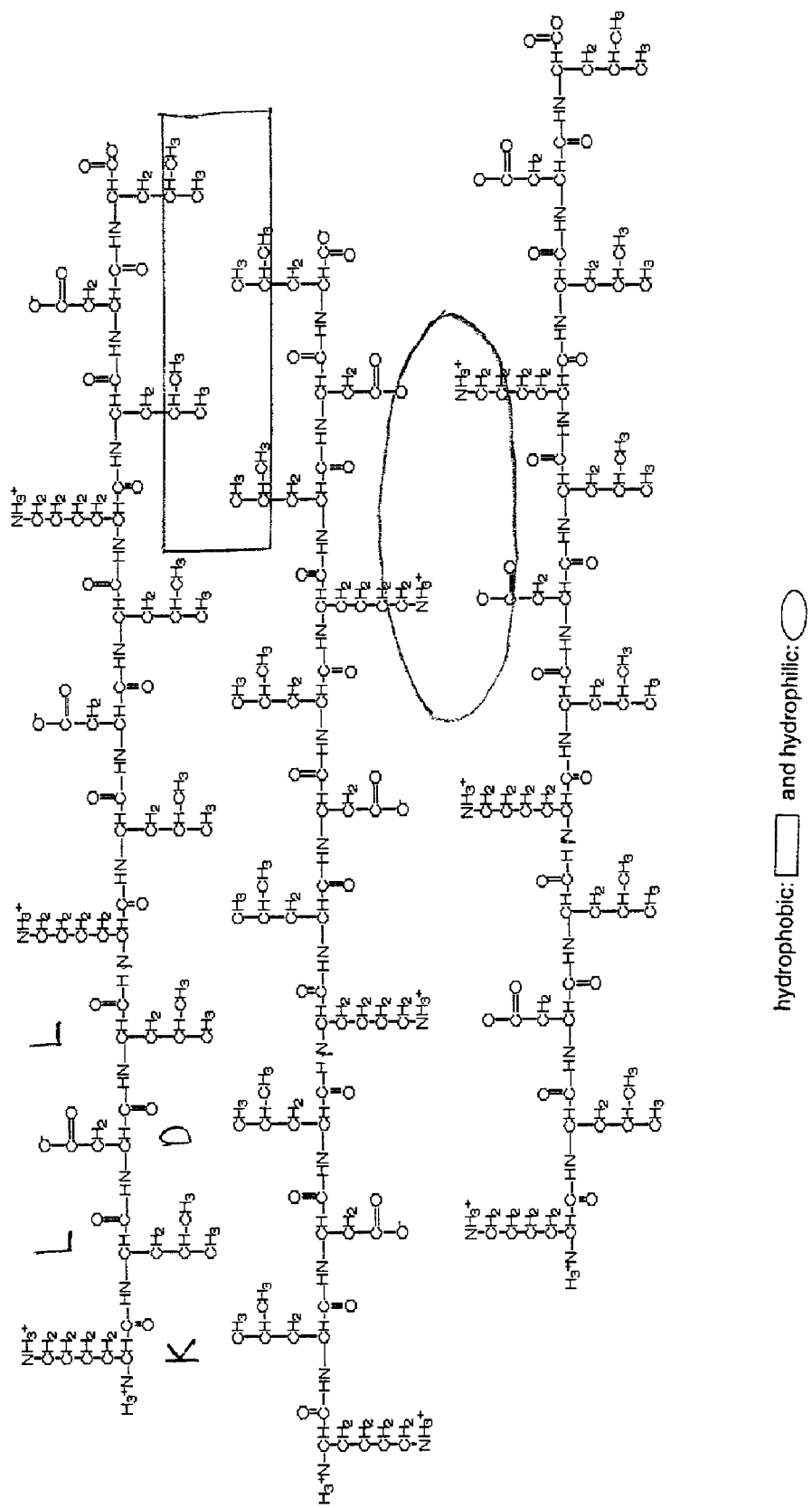
FIG. 1 is a schematic illustration of the interactions between peptides in the peptide scaffold. Various peptides with amino acid sequences of alternating hydrophobic and hydrophilic residues self-assemble to form a stable scaffold of beta-sheets when exposed to physiologically-equivalent electrolyte solutions (U.S. Pat. Nos. 5,955,343 and 5,670,483). The peptide scaffolds are stabilized by numerous interactions between the peptides. For example, the positively charged and negatively charged amino acid side chains from adjacent peptides form complementary ionic pairs, and other hydrophilic residues such as asparagine and glutamine participate in hydrogen-bonding interactions. The hydrophobic groups on adjacent peptides participate in van der Waals interactions. The amino and carbonyl groups on the peptide backbone also participate in intermolecular hydrogen-bonding interactions.

To maintain their phenotype, chondrocytes are typically cultured in a three-dimensional environment. Within such an arrangement, chrondrocytes develop a mechanically functional extracellular matrix and respond appropriately to static and dynamic compressive loads. We have discovered that a peptide scaffold that encapsulates living cells in a three-dimensional arrangement may be formed by first mixing the cells and the peptides in a solution having the required osmolarity to maintain cell viability, and then adding sufficient electrolytes to initiate self-assembly of the scaffold. Long-term cultures showed that the chondrocytes encapsulated by this scaffold deposited a continuous matrix, maintained a rounded morphology, and had a significant rate of protein and proteoglycan synthesis. These results indicate that a peptide gel scaffold encapsulating chondrocytes may be used to repair or replace cartilage tissue.

Secretion of extracellular matrix components by the encapsulated chondrocytes increased the equilibrium modulus, a measure of the strength of the scaffold, by over 50-fold by day 28 after scaffold formation. If desired, the stiffness of the scaffold may be further increased by incorporating cysteines which may be disulfide bonded or by incorporating aromatic residues which may be UV cross-linked into the scaffold. In addition, varying the length or concentration of the peptides may further increase the stiffness of the scaffold. Moreover, forming the scaffolds in the presence of growth factors so that they are encapsulated by the scaffold, adding growth factors to the media surrounding the scaffold so that they diffuse into the scaffold, or using standard molecular biology techniques to modify the encapsulated cells so that they express heterologous growth factors or over-express endogenous growth factors is expected to promote the proliferation of the encapsulated cells and to increase the secretion of extracellular matrix components by the cells. Moreover, subjecting the scaffold to external pressure may further enhance the secretion of extracellular matrix components by the cells, resulting in an even higher equilibrium modulus. Also, the stiffness of the scaffold may further increase after it is implanted in vivo. Thus, the equilibrium compression modulus of the peptide scaffold may approach the 500 kPA value of articular cartilage.

Because these peptide scaffolds have been previously shown to be nontoxic to a variety of mammalian cell types, the methods of the present invention may also be applied to other cell types for applications involving other tissue types (Zhang et al., Biomaterials 16:1385-1393, 1995). The strength of scaffolds that is required to repair or replace soft tissues such as young male thigh and forearm skin which have equilibrium compression moduli of 1.99 and 1.51 kPa, respectively, is much lower than that required for cartilage. Additionally, neurons grown in a monolayer on the outside surface of a peptide scaffold have been previously shown to exhibited extensive neurite outgrowth. Thus, neurons that are encapsulated by these peptide scaffolds using the methods of the present invention may project axons that enable cell-to-cell contact between the encapsulated cells and neighboring endogenous neurons.

The following examples are to illustrate the invention. They are not meant to limit the invention in any way.

Peptide Scaffolds

Certain peptides consisting of alternating hydrophilic and hydrophobic amino acids self-assemble to form an exceedingly stable beta-sheet macroscopic scaffold in the presence of electrolytes, such as monovalent alkaline cations (U.S. Pat. Nos. 5,955,343 and 5,670,483). For example, NaCl at a concentration of between 5 mM and 5 M induces the assembly of scaffolds within a few minutes. Lower concentrations of NaCl may also induce assembly but at a slower rate. The side-chains of the peptides in the scaffold partition into two faces, a polar face with charged ionic side chains and a non-polar face with alanines or other hydrophobic groups. These ionic side chains are self-complementary to one another in that the positively charged and negatively charged amino acid residues can form complementary ionic pairs. These peptides are therefore called ionic self-complementary peptides, or Type I self-assembling peptides. If the ionic residues alternate with one positively and one negatively charged residue (−+−+−+−+), the peptides are described as "modulus I;" if the ionic residues alternate with two positively and two negatively charged residues (−−++−−++), the peptides are described as "modulus II."

Many modulus I and II self-complementary peptides with identical compositions and length; such as EAK16, KAE16, RAD16, RAE16, and KAD16; have been analyzed previously (Table 1). Modulus IV ionic self-complementary peptides containing 16 amino acids; such as EAK16-IV, KAE16-IV, DAR16-IV and RAD16-IV; have also been studied. If the charged residues in these self-assembling peptides are substituted (i. e., the positive charged lysines are replaced by positively charged arginines and the negatively charged glutamates are replaced by negatively charged aspartates), there are essentially no significant effects on the self-assembly process. However, if the positively charged resides, lysine and arganine are replaced by negatively charged residues, aspartate and glutamate, the peptides can no longer undergo self-assembly to form macroscopic scaffolds; however, they can still form a beta-sheet structure in the presence of salt. Other hydrophilic residues, such as asparagine and glutamine, that form hydrogen-bonds may be incorporated into the peptides instead of, or in addition to, charged residues. If the alanines in the peptides are changed to more hydrophobic residues, such as leucine, isoleucine, phenylalanine or tyrosine, these peptides have a greater tendency to self-assemble and form peptide matrices with enhanced strength. Some peptides that have similar compositions and lengths as the aforementioned peptides form alpha-helices and random-coils rather than beta-sheets and do not form macroscopic structures. Thus, in addition to self-complementarity, other factors are likely to be important for the formation of macroscopic scaffolds, such as the peptide length, the degree of intermolecular interaction, and the ability to form staggered arrays.

TABLE 1

Representative Self-Assembling Peptides

| Name | Sequence (n-->c) | Modulus | Structure |
|---|---|---|---|
| RADA16-I | n-RADARADARADARADA-c | I | β |
| RGDA16-I | n-RADARGDARADARGDA-c | I | r.c. |
| RADA8-I | n-RADARADA-c | I | r.c. |
| RAD16-II | n-RARADADARARADADA-c | II | β |
| RAD8-II | n-RARADADA-c | II | r.c. |
| EAKA16-I | n-AEAKAEAKAEAKAEAK-c | I | β |
| EAKA8-I | n-AEAKAEAK-c | I | r.c. |
| RAEA16-I | n-RAEARAEARAEARAEA-c | I | β |
| RAEA8-I | n-RAEARAEA-c | I | r.c. |
| KADA16-I | n-KADAKADAKADAKADA-c | I | β |
| KADA8-I | n-KADAKADA-c | I | r.c. |
| EAH16-II | n-AEAEAHAHAEAEAHAH-c | II | β |
| EAH8-II | n-AEAEAHAH-c | II | r.c. |
| EFK16-II | n-FEFEFKFKFEFEFKFK-c | II | β |
| EFK8-II | n-FEFKFEFK-c | I | β |

TABLE 1-continued

Representative Self-Assembling Peptides

| Name | Sequence (n-->c) | Modulus | Structure |
|---|---|---|---|
| ELK16-II | n-LELELKLKLELELKLK-c | II | β |
| ELK8-II | n-LELELKLK-c | II | r.c. |
| EAK16-II | n-AEAEAKAKAEAEAKAK-c | II | β |
| EAK12 | n-AEAEAEAEAKAK-c | IV/II | α/β |
| EAK8-II | n-AEAEAKAK-c | II | r.c. |
| KAE16-IV | n-KAKAKAKAEAEAEAEA-c | IV | β |
| EAK16-IV | n-AEAEAEAEAKAKAKAK-c | IV | β |
| RAD16-IV | n-RARARARADADADADA-c | IV | β |
| DAR16-IV | n-ADADADADARARARAR-c | IV | α/β |
| DAR16-IV* | n-DADADADARARARARA-c | IV | α/β |
| DAR32-IV | n-(ADADADADARARARAR)-c | IV | α/β |
| EHK16 | n-HEHEHKHKHEHEHKHK-c | N/A | r.c. |
| EHK8-I | n-HEHEHKHK-c | N/A | r.c. |
| VE20* | n-VEVEVEVEVEVEVEVEVEVE-c | N/A | β |
| RF20* | n-RFRFRFRFRFRFRFRFRFRF-c | N/A | β |

β denotes beta-sheet;
α denote alpha-helix;
r.c. denotes random coil;
N/A denotes not applicable.
*Both VE20 and RF20 form a beta-sheet when they are incubated in a solution containing NaCl; however, they do not self-assemble to form macroscopic scaffolds.

Other self-assembling peptides may be generated by changing the amino acid sequence of any self-assembling peptide by a single amino acid residue or by multiple amino acid residues. Additionally, the incorporation of specific cell recognition ligands, such as RGD or RAD, into the peptide scaffold may promote the proliferation of the encapsulated cells. In vivo these ligands may also attract cells from outside a scaffold to the scaffold, where they may invade the scaffold or otherwise interact with the encapsulated cells. To increase the mechanical strength of the scaffolds, cysteines may be incorporated into the peptides to allow the formation of disulfide bonds, or residues with aromatic rings may be incorporated and cross-linked by exposure to UV light. The in vivo half-life of the scaffolds may also be modulated by the incorporation of protease cleavage sites into the scaffold, allowing the scaffold to be enzymatically degraded. Combinations of any of the above alterations may also be made to the same peptide scaffold.

Peptides capable of being cross-linked may be synthesized using standard f-moc chemistry and purified using high pressure liquid chromatography (Table 2). The formation of a peptide scaffold may be initiated by the addition of electrolytes as described herein. The hydrophobic residues with aromatic side chains may be crossed linked by exposure to UV irradiation. The extent of the cross-linking may be precisely controlled by the predetermined length of exposure to UV light and the predetermined peptide concentration. The extent of cross-linking may be determined by light scattering, gel filtration, or scanning electron microscopy using standard methods. Furthermore, the extent of cross-linking may also be examined by HPLC or mass spectrometry analysis of the scaffold after digestion with a protease, such as matrix metalloproteases. The material strength of the scaffold may be determined before and after cross-linking, as described herein.

TABLE 2

Representative Peptides for Cross-Linking Study

| Name | Sequence (N-->C) |
|---|---|
| RGDY16 | RGDYRYDYRYDYRGDY |
| RGDF16 | RGDFRFDFRFDFRGDF |
| RGDW16 | RGDWRWDWRWDWRGDW |
| RADY16 | RADYRYEYRYEYRADY |
| RADF16 | RADFRFDFRFDFRADF |
| RADW16 | RADWRWDWRWDWRADW |

Aggrecan processing sites, such as those underline in Table 3, may be added to the amino- or carboxy-terminus of the peptides or between the amino- and carboxy-termini. Likewise, other matrix metalloproteases (MMPs) cleavage sites, such as those for collagenases, may be introduced in the same manner. Peptide scaffolds formed from these peptides, alone or in combination with peptides capable of being cross-linked, may be exposed to various protease for various lengths of time and at various protease and scaffold concentrations. The rate of degradation of the scaffolds may be determined by HPLC, mass spectrometry, or NMR analysis of the digested peptides released into the supernatant at various time points. Alternatively, if radiolabeled peptides are used for scaffold formation, the amount of radiolabeled peptides released into the supernatant may be measured by scintillation counting.

TABLE 3

Representative Peptides for Enzymatic Cleavage Study

| Name | Sequence (N-->C) |
|---|---|
| REEE | RGDYRYDYTFREEE-GLGSRYDYRGDY |
| KEEE | RGDYRYDYTFKEEE-GLGSRYDYRGDY |
| SELE | RGDYRYDYTASELE-GRGTRYDYRGDY |
| TAQE | RGDYRYDYAPTAQE-AGEGPRYDYRGDY |
| ISQE | RGDYRYDYPTISQE-LGQRPRYDYRGDY |
| VSQE | RGDYRYDYPTVSQE-LGQRPRYDYRGDY |

Figure 9:
FIGS. 9A-9C are pictures of peptide scaffolds formed in a variety of predetermined shapes, including a tape (FIG. 9A), a rope (FIG. 9B), and a sheet (FIG. 9C) (Holmes et al., PNAS 97:6728-6733, 2000). To form a tape-shaped macroscopic peptide scaffold, the RAD16-II peptide was dissolved in water and injected through a device, which consisted of two pieces of thin wire spaced 5 mm apart and sandwiched between two glass slides, into phosphate-buffered saline (PBS). The scaffold was then stained with Congo red. The tape shown in FIG. 9A is approximately 8 cm in length, 0.5 cm in width, and 0.3 mm in thickness. A similar procedure was also used to form a peptide scaffold in the shape of a rope. In this case, the aqueous peptide solution was introduced into PBS using a 3-mL syringe. The peptide scaffold rope shown in FIG. 9B is 18 cm in length and 2 mm in diameter.
Figure 9:
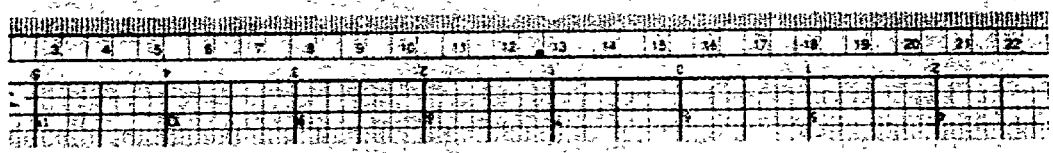
Figure 9:

If desired, peptide scaffolds may also be formed with a predetermined shape or volume (FIGS. 9A-9C). To form a scaffold with a desired geometry or dimension, an aqueous peptide solution is added to a pre-shaped casting mold, and the peptides are induced to self-assemble into a scaffold by the addition of an electrolyte, as described herein. The resulting geometry and dimensions of the macroscopic peptide scaffold are governed by the concentration and amount of peptide solution that is applied, the concentration of electrolyte used to induce assembly of the scaffold, and the dimensions of the casting apparatus.

If desired, the peptide scaffolds formed from any of the above peptides may be characterized using various biophysical and optical instrumentation, such as circular dichroism (CD), dynamic light scattering, Fourier transform infrared (FTIR), atomic force microscopy (ATM), scanning electron microscopy (SEM), and transmission electron microscopy (TEM) (see, for example, Leon et al., supra; Holmes et al. (2000), supra). For example, biophysical methods may be used to determine the degree of beta-sheet secondary structure in the peptide scaffold. Additionally, filament and pore size, fiber diameter, length, elasticity, and volume fraction may be determined using quantitative image analysis of scanning and transmission electron microscopy. The scaffolds may also be examined using several standard mechanical testing techniques to measure the extent of swelling, the effect of pH and electrolyte concentration on scaffold formation, the level of hydration under various conditions, and the tensile strength.

Peptide Scaffold Encapsulating Chondrocytes

A peptide with the amino acid sequence n-KLDLKLD-LKLDL-c (KLD12) was synthesized using a peptide synthesizer (Applied Biosystems) and lyophilized to a powder. A 0.5% peptide casting solution was obtained by dissolving KLD12 in a solution of 295 mM sucrose and 1 mM HEPES. Freshly isolated chondrocytes from bovine calf femoropatellar groove cartilage were re-suspended in the casting solution at a concentration of $15 \times 10^6$ cells/ml. The suspension was injected into a casting frame consisting of a 40×40×1.5 mm window supported on both faces by filter paper and a porous mesh. The casting frame was placed in a 1× phosphate-buffered saline (PBS, which contains 150 mM NaCl and 10 mM sodium phosphate at pH 7.4) bath for 15 minutes to induce the self-assembly of the peptides into a scaffold. Preferably, the cells are incubated in the sucrose solution for less than 5 minutes, or more preferably for less than 1 minute, before PBS is added. If desired, formation of a peptide scaffold may be confirmed using phase-contrast microscopy. As a control, cells were also suspended into warm agarose (2% solution, w/w), injected into the casting frame, and placed into a cold 1× PBS bath for 5 minutes. Both the peptide and control agarose gels were maintained in DMEM media (Gifco) plus 10% FBS, which was changed every other day.

Initial cell viability was determined based on ethidium bromide staining using a standard FDA assay (Jones et al., Journal of Histochemistry and Cytochemistry 33(1):77-79, 1985; Beletsky et al., Journal of Immunological Methods 134(2):201-205, 1990). For both the peptide scaffold and the agarose gel, initial cell viability was comparable (80-95% after two hours and approximately 75% after 24 hours).

For the following studies of protein and proteoglycan synthesis, glycosaminoglycan (GAG) accumulation, and immunohistochemistry, a 3 mm diameter by 1.5 mm thick cylindrical plug was punched immediately prior to addition of a radiolabel, digestion, or fixation. Extracellular protein production in a plug from the scaffold was measured by addition of [$^3$H]-proline to the media. The radiolabeled proline was taken up by the cells and incorporated into newly synthesized proteins. After 16-24 hours in the radiolabeled media, the plug was rinsed with buffer to remove free [$^3$H]-proline. The extracellular protein was digested by incubation in a proteinase K solution overnight at approximately 60° C., and the radioactivity present in the digested protein was quantitated by scintillation counting. Proteoglycan production was measured similarly, except that [$^{35}$S]-sulfate was added to the media instead of [$^3$H]-proline. The total accumulation of GAG, a proteoglycan component, was measured based on fluorometric analysis of the amount of DMMB dye bound (Chandrasekhar et al., Analytical Biochemistry 161(1): 103-

Figure 2:
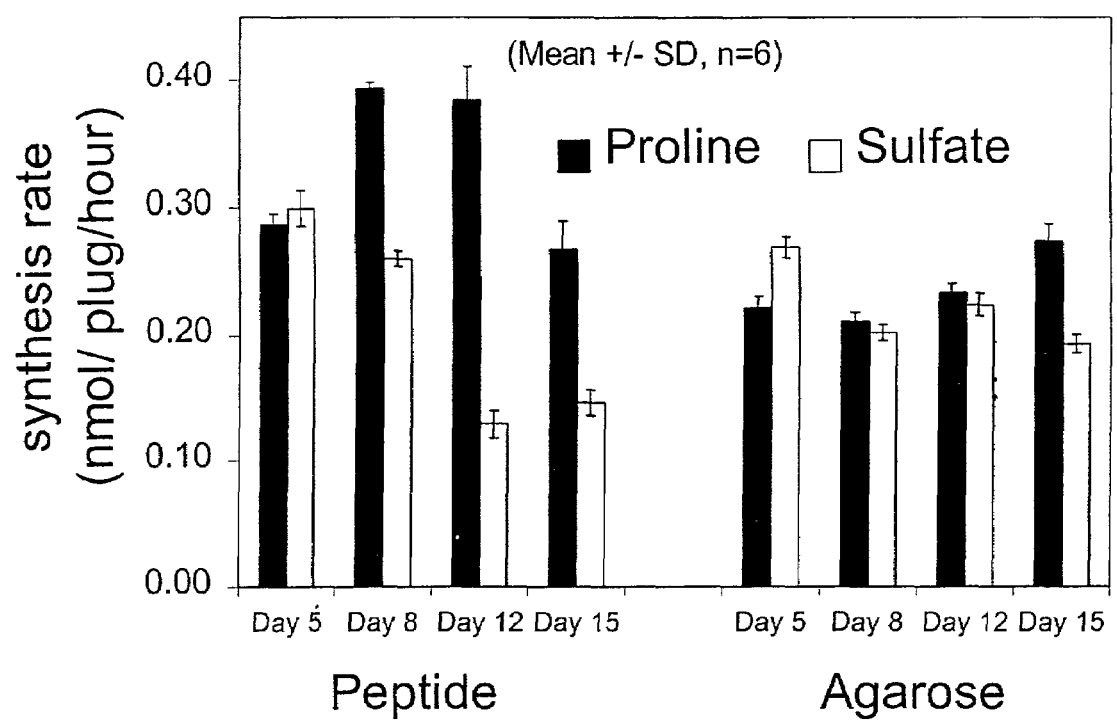
FIG. 2 is a bar graph showing the rates of protein and proteoglycan synthesis in chrondrocytes encapsulated by a peptide scaffold compared to the corresponding rates in chrondrocytes suspended in an agarose gel.
Figure 3:
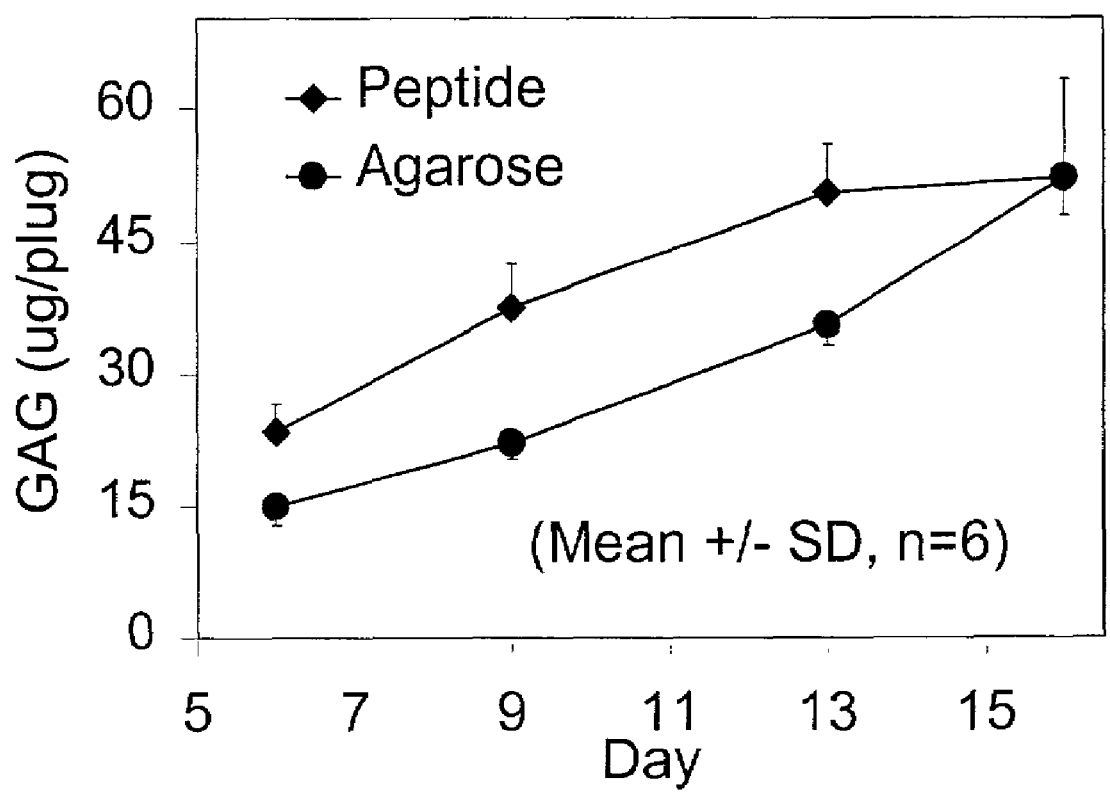
FIG. 3 is a graph showing the amount of glycosaminoclycan (GAG) synthesized by chrondrocytes encapsulated by a peptide scaffold or suspended in an agarose gel.

108, 1987). The rates of protein and proteoglycan synthesis by the cells in the peptide scaffold were similar to the rates by cells in the agarose gel (FIG. 2). As total GAG accumulation increased (based on measurements of DMMB binding, FIG. 3), the rate of GAG synthesis decreased (based on radiolabel incorporation, FIG. 2), as seen previously.

Figure 4:
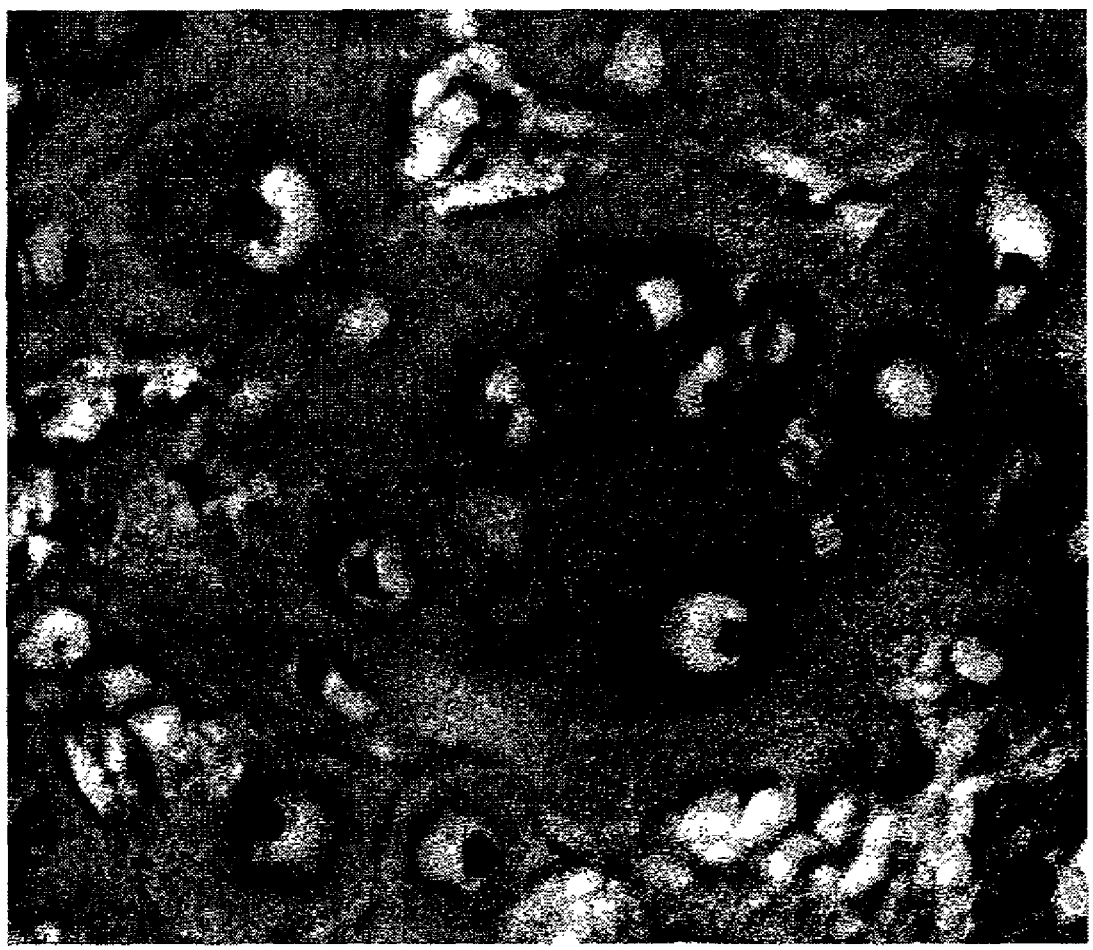
FIG. 4 is a picture of the toluidine blue staining of glycosaminoclycan in a peptide scaffold encapsulating chondrocytes.
Figure 5:
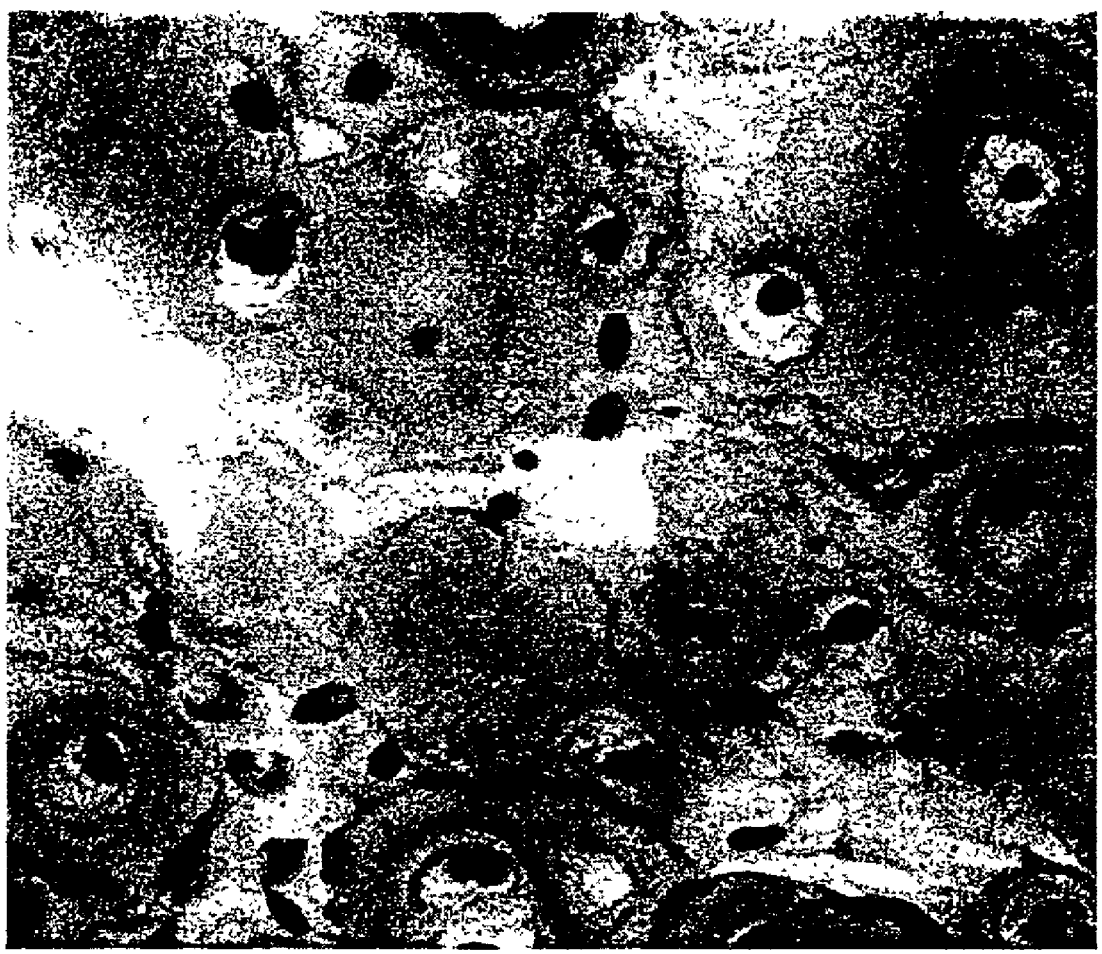
FIG. 5 is a picture of immunohistochemical staining for collagen II in a peptide scaffold encapsulating chondrocytes.

For histological analysis of GAG, collagen I, and collagen II, samples were fixed at day 21. To visualize GAG, toluidine blue dye was applied using standard procedures (FIG. 4). Based on this staining, proteoglycan deposition is present throughout the gel, with higher intensity in the pericellular regions. Immunohistochemical staining of collagen I using standard procedures resulted in light background staining throughout the gel, with no increase in the pericellular region (Ioannidis et al., Cell Tissue Res. 297:141-147, 1999; Domm et al., Orthopäde 29:91-99, 2000). Collagen II staining with DMP showed a similar deposition pattern as that of GAG staining but with less defined pericellular staining (Ioannidis et al., supra; Domm et al., supra) (FIG. 5). This result is consistent with the known lower pericellular deposition of collagen.

Figure 6:
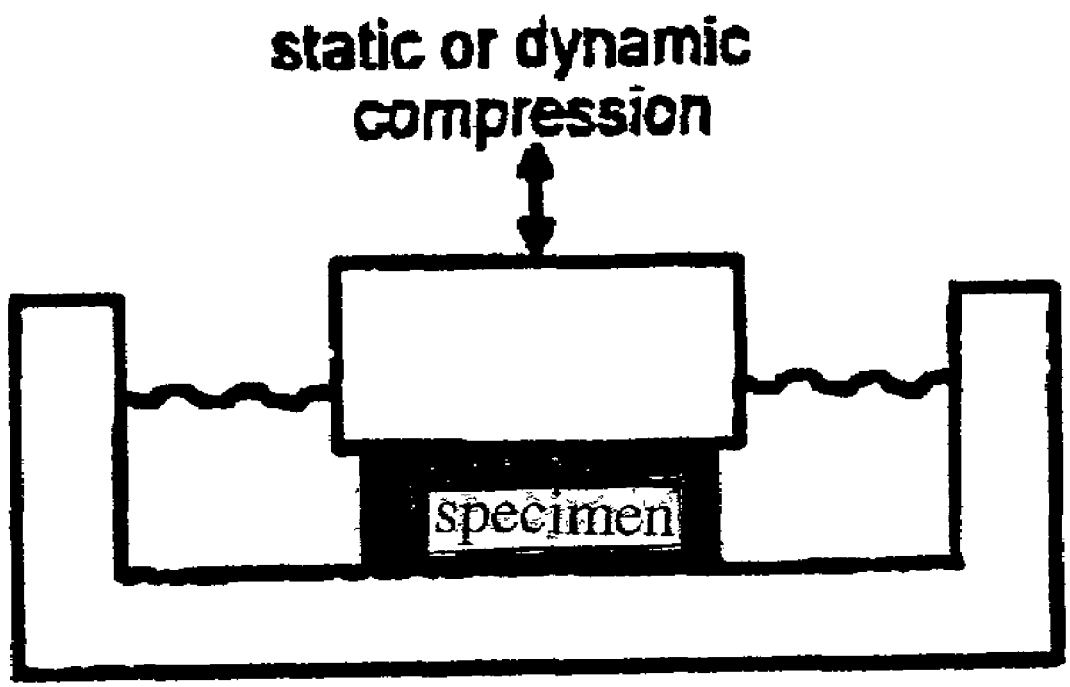
FIG. 6 is a schematic illustration of the apparatus used for mechanical testing of peptide scaffolds and that may be used, if desired, to compress the scaffolds to stimulate the secretion of extracellular matrix components by the encapsulated cells (Buschmann et al., J. of Cell Science 108:1497-1508, 1995)
Figure 7:
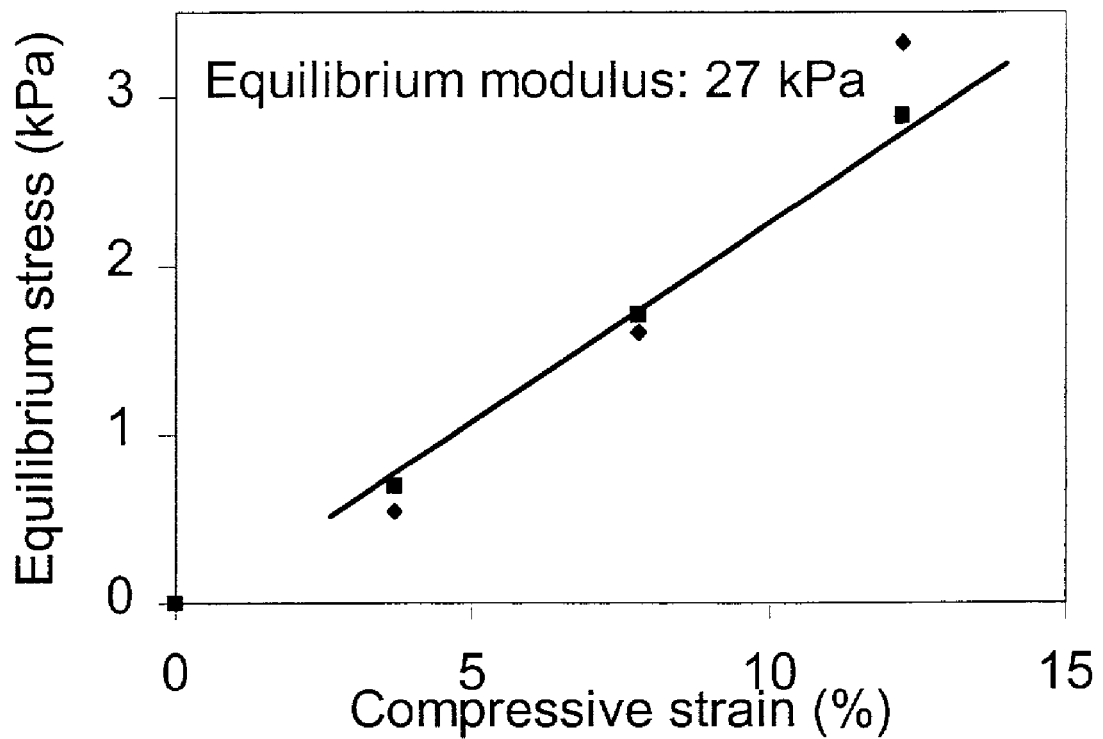
FIG. 7 is a graph of the equilibrium stress values at different compressive strain values for the peptide scaffold encapsulating chrondrocytes. Based on this graph, a equilibrium modulus of 27 kPa was calculated, which is significantly higher than the equilibrium modulus of approximately 0.5 kPa in the absence of cells.

For mechanical testing of the peptide scaffold, a 6 mm diameter by 1.5 mm thick cylindrical plug was taken from the scaffold at day 28. The plug was subjected to various levels of compression and the level of stress was measured, as described previously (Buschmann et al., supra). (FIGS. 6 and 7). Based on these results, the equilibrium modulus for the scaffold containing chondrocytes was 27 kPa compared to only approximately 0.5 kPa for a scaffold without cells or a scaffold immediately after encapsulation of chondrocytes. If desired, the stiffness of the peptide scaffolds may be further increased by subjecting the scaffold to static or dynamic compression using standard methods, such as those described by Buschmann et al. (supra). For example, dynamic compression at 0.01 to 3 Hz, superimposed on a static offset compression may be used. Typically, the dynamic strain amplitude is between 0.01 and 10%, and the static offset compression is between 5 and 15%.

Figure 8:
FIG. 8 is a picture showing the distribution of chondrocytes five days after scaffold formation. Each cluster or pair of cells evolved from one cell and is substantially uniformly dispersed.

The above method for encapsulating chondrocytes in a peptide scaffold was also repeated using a lower initial cell density of approximately $0.5 \times 10^6$ cells/mL. After formation of the peptide scaffold, the cells were substantially evenly dispersed in the scaffold, and cell viability was approximately 80% at 24 hours after scaffold formation. As illustrated in FIG. 8, pairs and clusters of cells that originated from a single cell were also substantially uniformly dispersed in the scaffold five days after its formation. In addition, the total number of cells increased approximately three-fold by day 5.

Other self-assembling peptides may be used in this method to encapsulate living chondrocytes or other cell types. If desired, the potential cytotoxicity of various peptide scaffolds may also be determined by measuring the rate of $^3$H-thymidine incorporation due to DNA replication or the rate of RNA expression of genes, such as actin or tubulin. Alternatively, a specific marker gene, such as enhanced green fluorescent protein under a specific promoter control, may be introduced into the cells to facilitate monitoring of gene expression and cell viability. The expression of proteins (e.g., fibronectin and fibronectin receptors) may also be analyzed using specific antibodies (see, for example, Ausubel et al., Current Protocols in Molecular Biology, Chapter 9, John Wiley & Sons, New York, 2000).

In Vivo Immune and Inflammatory Responses

The in vivo immune and inflammatory responses to two self-assembling peptides were analyzed. Neither the RAD16 or EAK16 peptides, alone or conjugated with other highly immunogeneic proteins such as BSA, elicited a detectable immunological response when injected into rabbits or goats (Holmes et al. (2000), supra). Also no significant titers of antibodies were obtained. To measure the inflammatory response elicited by these peptides, the peptides were injected into the leg muscle and brain of rats (Holmes et al. (2000), supra). No inflammation in these or neighboring areas was observed during the two weeks following the injection. Other self-assembling peptides may be tested similarly to measure the immune and inflammatory responses that they generate.

The lack of an immune or inflammatory response to these peptides in a variety of mammals suggests that the peptides may not elicit an adverse immune or inflammatory response when administered to humans. Furthermore, structural modeling and theoretical analysis of peptide presentations by class I and class II MHC molecules also suggest that the self-assembling peptides of the present invention are not likely to elicit strong immune response due to their alternating distribution of charged and uncharged residues.

In Vivo Animal Model Studies

Several previous studies have employed a canine model to compare the reparative tissues formed in defects in articular cartilage (see, for example, Brittberg et al., New England J. of Med. 331:889-894, 1994; Breinan et al., J. Bone Jt. Surg. 79-A: 1439-1451, 1997; Breinan et al. Tiss. Engr. 4:101-114, 1998; Nehrer et al., Biomaterials 19:2313-23128, 1998). For initial studies, four dogs are tested for each peptide scaffold. Two defects are made in each knee, and each defect is filled with a peptide scaffold encapsulating chondrocytes. Because previous studies have generated data on untreated control groups, an untreated control group is not needed for this study (Breinan et al. (1997), supra). However, if desired, dogs in which one or more of the knee detects are not filed with a scaffold or are filed with a scaffold that does not contain cells may be used as controls.

The power calculation for determining the required sample size for these experimental groups is based on detecting a 30% difference in the mean values of total fill, the areal percentage of hyaline cartilage, and the values of specific mechanical properties, assuming a 25% standard deviation. A 30% change in the outcome variable is expected to be a meaningful indication of the benefit of one treatment group over another. For a power of 0.80 ($\beta=0.20$) and a level of significance of $\alpha=0.05$, n=8 specimens are required. The statistical analysis is performed by averaging the values for the two defects in the same knee and counting the average value as one observation. However, in our previous work with this animal model, there were no systematic relationships between the two defects in the same knee of an animal. Thus, if desired, the individual defects may be treated as independent observations.

For this study, adult mongrel or hound dogs, each weighing approximately 25-30 kilograms, are used. Prior to the operation, the knee joints are examined roentgenographically to exclude animals with degenerative joint disease. All operations are performed under general anesthesia and sterile conditions, as described previously (Breinan et al. (1997), supra). Two 4 mm diameter defects are created in the trochlear groove of the right stifle (knee) joint. These defects are placed approximately 1.25 and 2.25 centimeters proximal to the intercondylar notch, each slightly lateral or medial to the midline. A 4 mm diameter dermal punch is used to outline the defect. Using loupe visualization, an attempt is made to remove all non-calcified cartilage from the defect by scraping the calcified cartilage surface with a customized curette, without fissuring the calcified cartilage. The objective is to remove all of the articular cartilage and to gently scrape the calcified cartilage to facilitate the integration of the reparative tissue with the calcified cartilage. A peptide scaffold with or without encapsulated chondrocytes is placed in each defect. Before closing the capsule, bleeding vessels are clamped and cauterized. The knee joint is closed by zero point suturing. Postoperatively, the operative knee are immobilized by external fixation (IMEX Veterinary, Longview, Tex.) for ten days (Breinan et. al. (1997), supra). It is also contemplated that the operative knee may be mobilized for a longer time period if required for the peptide scaffold to increase in stiffness as extracelluar matrix components are secreted in vivo by the encapsulated cells and/or nearby cells. Six months after the first surgical procedure, two defects are made in the left knee using the same procedure. The dogs are sacrificed 12 months after the initial surgical procedure, producing a postoperative evaluation period of 12 months for the right knees and six months for the left knees. It is also contemplated that other postoperative periods may be used, such as a few hours, a few days, or even a few years. Additionally, the defects in other dogs may be analyzed at earlier time points, such as after 30 minutes, a few hours, or a few days, to determine if early displacement of the graft is occurring.

After formalin fixation, specimens are immersed in a 15% disodium ethylenediamine tetracetate decalcifying solution at pH 7.4. The samples are placed on a shaker at 4° C. for four weeks, and during this incubation the decalcifying solution is changed every week. Samples are rinsed thoroughly, dehydrated, and embedded in paraffin at 60° C. Seven-micrometer thick sections are stained with hematoxylin, eosin, and/or safranin O/fast green. Selected paraffin sections are stained with antibodies to type I collagen and type II collagen.

The specific tissue types filling the defects are determined by evaluating the percentage of the area of the central section through the defect occupied by each tissue type: articular cartilage, non-articular hyaline cartilage, fibrocartilage, and fibrous tissue (Breinan et al. (1997), supra). These percentages refer only to the representative histological cross-section through the middle portion of the defect. They do not imply values equivalent to the actual volume percentages of tissues in the defects. Due to edge effects (regenerating tissues tend to form at the periphery of the defect), only sections representing 60% or more of the defect diameter are analyzed. Sections taken too close to the edge of the defect may preferentially show regeneration, which could yield misleading data. The effects of treatment and time on the areal percentages of specific tissue types are determined by two-way ANOVA. Group comparisons are made using the Student t test with the appropriate corrections.

Additionally, any degradation of adjacent tissues and the bonding of the repaired tissue to the subchondral plate and the adjacent cartilage may be evaluated. The presence of new tissue formed in the remodeling subchondral bone underlying the defects may also be determined, and the area surrounding the defects may be analyzed for signs of inflammation. If desired, the rate of scaffold degradation may be measured. For this determination of the in vivo degradation rate, radiolabelled peptides, such as $^{14}$C-, $^{3}$H-, or $^{35}$S-labelled peptides, may be assembled into a radiolabelled peptide scaffold and administered to a mammal using the methods of the present invention. At one or more time points after administration of the radioactive scaffold, urine or blood samples are obtained from the mammal. The amount of radioactivity in the sample is measured to determine the amount of degradation products that have been released from the scaffold.

Other animal models may be used to test peptides scaffolds encapsulating living cells for the ability to repair or replace tissues in vivo. For example, scaffold encapsulating chondrocytes may also be tested using rabbit models of cartilage defects (see, for example, Perka et al. Clinical Orthopaedics 378:245-254, 2000; Solchaga et al., Journal of Orthopaedic Research 18(5):773-780, 2000). Standard bone tissue engineering animal models may be used for in vivo studies of scaffolds encapsulating cells such as osteocytes (see, for example, Lennon et al., Experimental Cell Research 219(1): 211-222, 1995; Solchaga et al., supra; Boyan et al., Journal of Orthopaedic Research 17(2):246-55, 1999). Examples of ligament tissue engineering animal models that may be used to test peptide scaffolds for the ability to repair or replace ligament tissue in vivo include those described by Awad et al. (Tissue Engineering 5(3):267-277, 1999) and Kato et al. (Journal of Bone and Joint Surgery (Am) 73(4):561-574, 1991). Peptides scaffolds encapsulating any other cell type may also be routinely tested in an appropriate animal model. Standard medical procedures may be used to adapt the methods used to repair or replace tissues in these animal models for the treatment of other mammals, such as humans.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth.

What is claimed is:

1. A macroscopic scaffold comprising amphiphilic peptides and living cells, wherein said peptides have alternating hydrophobic and hydrophilic amino acids comprise multiple KLD subunits, are complementary and structurally compatible, and self-assemble into a beta-sheet macroscopic scaffold; and wherein said macroscopic scaffold is formed by the peptides self-assembling to encapsulate the living cells, said cells being present within said macroscopic scaffold in a three-dimensional arrangement.

2. The macroscopic scaffold of claim 1, further encapsulating a therapeutically active compound or chemoattractant.

3. The macroscopic scaffold of claim 1, wherein said peptides comprise an adhesion site, growth factor binding site, growth factor, or sequence that provides targeting to a cell, tissue, organ, organ system, or site within an mammal.

4. The macroscopic scaffold of claim 1, wherein said living cells are neurons and said macroscopic scaffold allows axonal outgrowth by said neurons.

5. The macroscopic scaffold of claim 1, wherein said cells are chondrocytes, bone marrow cells, osteocytes, periosteal cells, perichondrial cells, fibroblasts, neuronal cells, hippocampal cells, epidermal cells, endothelial cells, keratinocytes, basal cells, spinous cells, granular cells, embryonic stem cells, ovarian cells, pancreatic cells, cervical cells, liver cells, or foreskin cells.

6. The macroscopic scaffold of claim 1, wherein said cells secrete extracellular matrix components.

7. The macroscopic scaffold of claim 6, wherein said secretion of extracellular matrix components increases the equilibrium compression modulus of said macroscopic scaffold by at least 50 fold.

8. The macroscopic scaffold of claim 1, wherein at least 60% of the encapsulated cells are in cell-cell contact with another encapsulated cell.

9. The macroscopic scaffold of claim 1, wherein said cells are chondrocytes.

10. The macroscopic scaffold of claim 6, wherein said secretion of extracellular matrix components increases the strength of said macroscopic scaffold.

11. The macroscopic scaffold of claim 6, wherein said secretion of extracellular matrix components increases the stiffness of said macroscopic scaffold.

12. The macroscopic scaffold of claim 6, wherein said secretion of extracellular matrix components increases the equilibrium compression modulus of said macroscopic scaffold.

13. The macroscopic scaffold of claim 12, wherein said secretion of extracellular matrix components increases the equilibrium compression modulus of said macroscopic scaffold by between 5-fold and 50-fold.

14. The macroscopic scaffold of claim 1, wherein said cells are autologous or allogeneic with respect to a subject.

15. The macroscopic scaffold of claim 1, wherein said macroscopic scaffold is pre-shaped to fit a tissue defect.

16. The macroscopic scaffold of claim 1, wherein said macroscopic scaffold is subjected to static or dynamic compression or a combination thereof.

17. The macroscopic scaffold of claim 1, wherein said macroscopic scaffold is formed from a casting solution containing cells at a concentration of between 0.5 million and 15 million per ml of volume.

18. The macroscopic scaffold of claim 1, wherein said cells divide after encapsulation within the macroscopic scaffold.

19. The macroscopic scaffold of claim 1, wherein said macroscopic scaffold is subjected to static or dynamic compression or a combination thereof, wherein the dynamic compression is applied at 0.01 to 3 Hz.

20. The macroscopic scaffold of claim 1, wherein said macroscopic scaffold has a predetermined shape or volume.

21. The macroscopic scaffold of claim 1, wherein the cells encapsulated in said macroscopic scaffold are substantially uniformly distributed therein.

22. The macroscopic scaffold of claim 1, wherein said macroscopic scaffold is formed by
   (a) incubating peptides and living cells in an aqueous solution comprising a predetermined concentration of a carbohydrate or glycerol and having sufficient osmolarity to maintain cell viability under conditions that do not allow the peptides to substantially self-assemble; and
   (b) adding an electrolyte to said solution sufficient to initiate self-assembly of said peptides into a beta-sheet macroscopic scaffold, whereby said cells are encapsulated by the formation of said macroscopic scaffold and are present in said macroscopic scaffold in a three-dimensional arrangement.

23. The macroscopic scaffold of claim 1, wherein said macroscopic scaffold is formed by
(a) incubating living cells in an aqueous solution comprising a predetermined concentration of a carbohydrate or glycerol and having sufficient osmolarity to maintain cell viability under conditions that do not allow the peptides to substantially self-assemble;
(b) mixing the aqueous solution containing living cells and with a peptide solution; and
(c) adding an electrolyte to the sufficient to initiate self-assembly of said peptides into a beta-sheet macroscopic scaffold to the solution resulting from step (b), whereby said cells are encapsulated by the formation of said macroscopic scaffold and are present in said macroscopic scaffold in a three-dimensional arrangement.

24. The macroscopic scaffold of claim 1, wherein said macroscopic scaffold is formed by
(a) dissolving peptides in a solution comprising a predetermined concentration of a carbohydrate or glycerol and having sufficient osmolarity to maintain cell viability under conditions that do not allow the peptides to substantially self-assemble;
(b) adding living cells to the solution containing the peptides; and
(c) adding an electrolyte to said solution sufficient to initiate self-assembly of said peptides into a beta-sheet macroscopic scaffold, whereby said cells are encapsulated by the formation of said macroscopic scaffold and are present in said macroscopic scaffold in a three-dimensional arrangement.

25. The macroscopic scaffold of claim 1, wherein said macroscopic scaffold is formed by
(a) incubating peptides and living cells in a solution comprising a predetermined concentration of a carbohydrate or glycerol and having sufficient osmolarity to maintain cell viability under conditions that do not allow the peptides to substantially self-assemble, wherein said solution is contained in a pre-shaped mold dimensioned to determine the volume or shape of said macroscopic scaffold; and
(b) adding an electrolyte to said solution sufficient to initiate self-assembly of said peptides into a beta-sheet macroscopic scaffold, whereby said cells are encapsulated by the formation of said macroscopic scaffold and are present in said macroscopic scaffold in a three-dimensional arrangement.

26. The macroscopic scaffold of claim 1, wherein said macroscopic scaffold is subjected to static or dynamic compression, or a combination thereof, sufficient to increase secretion by cells encapsulated therein.

* * * * *